United States Patent
Ray et al.

(10) Patent No.: US 12,292,448 B2
(45) Date of Patent: May 6, 2025

(54) QUANTITATIVE ANALYSIS OF PROTEINS

(71) Applicant: Sigma-Aldrich Co. LLC, St. Louis, MO (US)

(72) Inventors: Kevin B. Ray, Ballwin, MO (US); Pegah Jalili, St. Louis, MO (US); Jeffrey L. Turner, Maryville, IL (US); Nicolas Caffarelli, St. Louis, MO (US); Yue Lu, St. Louis, MO (US)

(73) Assignee: Sigma-Aldrich Co. LLC, St. Louis, MO (US)

( * ) Notice: Subject to any disclaimer, the term of this patent is extended or adjusted under 35 U.S.C. 154(b) by 1152 days.

(21) Appl. No.: 16/971,286

(22) PCT Filed: May 8, 2019

(86) PCT No.: PCT/US2019/031271
§ 371 (c)(1),
(2) Date: Aug. 19, 2020

(87) PCT Pub. No.: WO2019/226347
PCT Pub. Date: Nov. 28, 2019

(65) Prior Publication Data
US 2020/0378986 A1    Dec. 3, 2020

Related U.S. Application Data

(60) Provisional application No. 62/675,989, filed on May 24, 2018.

(51) Int. Cl.
| | |
|---|---|
| G01N 33/543 | (2006.01) |
| G01N 30/02 | (2006.01) |
| G01N 33/538 | (2006.01) |
| G01N 33/549 | (2006.01) |
| G01N 33/563 | (2006.01) |
| G01N 33/68 | (2006.01) |

(52) U.S. Cl.
CPC ......... *G01N 33/6848* (2013.01); *G01N 30/02* (2013.01); *G01N 33/538* (2013.01); *G01N 33/549* (2013.01); *G01N 33/563* (2013.01); *G01N 2030/027* (2013.01); *G01N 2333/976* (2013.01)

(58) Field of Classification Search
None
See application file for complete search history.

(56) References Cited

U.S. PATENT DOCUMENTS

| | | |
|---|---|---|
| 7,229,539 B1 | 6/2007 | Lee et al. |
| 8,580,533 B2 | 11/2013 | Bouvier et al. |
| 2005/0232929 A1 | 10/2005 | Kadkhodayan et al. |
| 2009/0286258 A1 | 11/2009 | Kaur et al. |
| 2012/0309040 A1 | 12/2012 | Madian et al. |
| 2014/0248603 A1 | 9/2014 | Eichmeyer et al. |
| 2015/0203532 A1* | 7/2015 | Godawat ............ C07K 1/16 435/208 |
| 2015/0225343 A1* | 8/2015 | Cheng ............ A61P 25/28 514/319 |
| 2016/0176954 A1* | 6/2016 | Ruike ............ A61P 29/00 435/254.2 |
| 2016/0327577 A1 | 11/2016 | Kushnir et al. |
| 2020/0033364 A1* | 1/2020 | Chen ............ C07K 16/40 |
| 2021/0148925 A1* | 5/2021 | Hoang ............ G01N 35/00 |

FOREIGN PATENT DOCUMENTS

| | | |
|---|---|---|
| CN | 105026419 A | 11/2015 |
| CN | 108700598 A | 10/2018 |
| EP | 3270154 A1 | 1/2018 |
| JP | 2013-531799 A | 8/2013 |
| JP | 2018506045 A | 3/2018 |
| KR | 10-2017-0121265 A | 11/2017 |
| WO | 03/087834 A2 | 10/2003 |
| WO | 2012/004371 A2 | 1/2012 |
| WO | 2015/033479 A1 | 3/2015 |
| WO | 2015/120036 A1 | 8/2015 |
| WO | 2016/094425 A1 | 6/2016 |
| WO | 2017/165734 A1 | 9/2017 |
| WO | 2018/183449 A1 | 10/2018 |

OTHER PUBLICATIONS

Diamandis et al., Immunoassay, Academic Press, Chapter 11, The Avidin-Biotin System, pp. 237-267, 1996 (Year: 1996).*
Mouchahoir et al., Development of an LC-MS/MS peptide mapping protocol for the NISTmAB, Analytical and Bioanalytical Chemistry, published only Feb. 2018, 410, pp. 2111-2126. (Year: 2018).*
Ladwig et al., Quntitation of the IgF2/4 kappa Monoclonal Therapeutic Eculizumab from Serum Using Isotype Specific Affinity Purification and Microflow LC-Esi-Q-TOF Mass Spectrometry, J. Am. Soc. Mass Specrom., 2017, 28, pp. 811-817. (Year: 2017).*
International Search Report and Written Opinion received for PCT Patent Application No. PCT/US2019/031271, mailed on Jul. 19, 2019, 12 pages.
Yuan, et al., "Simple and Efficient Digestion of a Monoclonal Antibody in Serum Using Pellet Digestion: Comparison with Traditional Digestion Methods in LC-MS/MS Bioanalysis", Bioanalysis, Dec. 2012, pp. 2887-2896.
Peng, et al., "Development and Validation of LC-MS/MS Method for the Quantitation of Infliximab in Human Serum", Chromatographia, Feb. 28, 2015, pp. 521-531.
Ouyang, et al., "Pellet Digestion: A Simple and Efficient Sample Preparation Technique for LC-MS/MS Quantification of Large Therapeutic Proteins in Plasma", Bioanalysis, Published Online: Dec. 23, 2011, pp. 17-28.
Office Action received for Chinese Patent Application No. 201980034937.1 mailing date May 25, 2023, 28 Pages (18 Pages of English translation & 10 Pages of official copy).

(Continued)

*Primary Examiner* — Gary Counts
(74) *Attorney, Agent, or Firm* — Sigma-Aldrich Co. LLC

(57) ABSTRACT

Methods and kits for detecting and/or quantitating target proteins in biological samples. In particular, the method comprises capture and immobilization of the target protein, protein denaturation, proteolytic digestion, and analysis using a mass spectrometry-based technique.

25 Claims, 3 Drawing Sheets

(56) References Cited

OTHER PUBLICATIONS

Office Action received for Chinese Patent Application No. 201980034937.1 mailing date Jan. 26, 2024, 30 Pages (18 Pages of English translation & 12 Pages of Official copy).
Kun, S. et al., "Collagen quantitation by detection of marker peptides with HPLC-MS", Chinese Journal of Biotechnology, vol. 31, No. 11, Nov. 25, 2015, pp. 1660-1668 (English Abstract Submitted).
Wang, K. et al., "Identification and Release Behavior of Wheat Germ Protein with Mass Spectrometry", The Chinese Journal of Process Engineering, vol. 16, No. 3, Jun. 2016, 5 Pages (English Abstract Submitted).
Office Action received for Chinese Patent Application No. 201980034937.1 mailing date Nov. 4, 2023, 23 pages (14 Pages of English Translation and 9 Pages of Official Copy).
Communication pursuant to Article 94(3) EPC received for European Patent Application No. 19728178.5 mailing date May 29, 2024, 5 Pages.

\* cited by examiner

QUANTITATIVE ANALYSIS OF PROTEINS

RELATED APPLICATIONS

The present application is a US National Stage application of International Application No. PCT/US2019/031271, filed May 8, 2019, which claims the benefit of priority of U.S. Provisional Application No. 62/675,989, filed May 24, 2018, the entirety content of each of which is incorporated herein by reference.

FIELD

The present disclosure relates to methods for detecting and/or quantitating proteins in complex biological samples.

BACKGROUND

Proteins and antibodies have emerged as key therapeutic agents and diagnostic biomarkers for a wide range of human diseases. It is therefore of growing importance to develop a robust bioanalytical assay that is able to quantify proteins in complex biological matrices such as serum and plasma, Immunoaffinity-mass spectrometry methods continue to gain popularity for such assays. To date, a wide range of literature citations report immunoaffinity-mass spectrometry methods for accurate quantification of proteins and antibodies. However, many methods utilize magnetic bead based formats for immunoaffinity enrichment, often followed by reduction and alkylation, overnight digestion, and post-digestion cleanup steps. The bead based formats are limited by high cost and require that careful attention be taken to avoid loss of beads during the washing steps and aspiration of beads during collection step to prevent blockage of liquid chromatography needles and columns. Thus, there is a need for cheaper, faster, and more sensitive high throughput analytical proteomic assays.

SUMMARY

Among the various aspects of the present disclosure is the provision of methods for detecting and/or quantitating target proteins in biological samples. The methods comprise (a) adding the biological sample to an immobilized antibody to capture the target protein, thereby forming an immobilized antibody-protein complex; (b) adding a denaturation solution comprising an organic solvent to the immobilized antibody-protein complex to form a denatured immobilized antibody-protein complex; (c) adding a digestion solution comprising a protease to the denatured immobilized antibody-protein complex to form a solution comprising proteolytic peptides; and (d) analyzing the solution comprising proteolytic peptides by a mass spectrometry-based technique to detect and/or quantitate the target protein in the biological sample, wherein the analysis utilizes at least one internal standard protein or peptide that is added during one step of the method.

Other aspects and iterations of the disclosure are described in more detail below.

DETAILED DESCRIPTION

Figure 1:
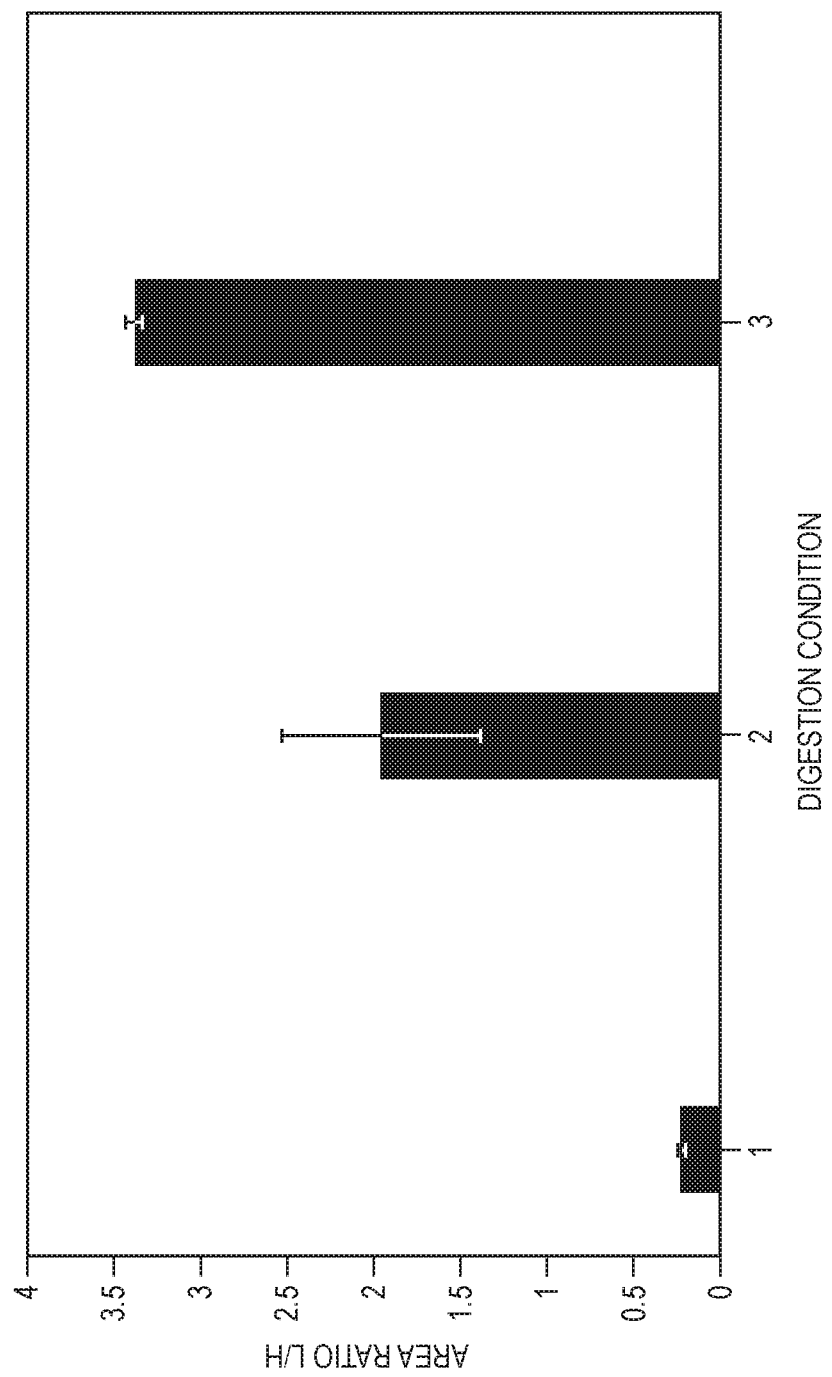
FIG. 1 shows the efficiency of digestion using three different digestion conditions/protocols, Protocol 1 was a rapid high temperature digestion without denaturation protocol, Protocol 2 was a convention reduction, alkylation, and overnight digestion at 37° C. Protocol 3 was the protocol disclosed herein, i.e., denaturation and rapid high temperature digestion.

The present disclosure provides methods for detecting and/or quantitating target proteins in complex biological samples, The methods utilize capture and enrichment of the target protein and a mass spectrometry-based analysis. In particular, the captured target protein is denatured by contact with an organic solvent prior to or during proteolytic digestion at an elevated temperature. The methods disclosed herein result in complete, consistent, reproducible proteolytic digestion, which is critical for accurate quantitation of proteins by mass spectrometry. As a consequence, the limit of quantitation of proteins is reduced about 10-fold relative to conventional proteomic methods.

(I) Methods For Detecting/Quantitating Proteins in Biological Samples

One aspect of the present disclosure encompasses methods for detecting and/or quantitating target proteins in complex biological samples. The method commences with a capture step during which a biological sample comprising the target proteins is contacted with immobilized capture entities, which bind and capture the target proteins from the biological sample, thereby forming immobilized target proteins. The next step of the method is a protein denaturation step during which the immobilized target proteins are contacted with a denaturation solution comprising an organic solvent to form denatured immobilized target proteins. The third step of the method comprises a proteolytic digestion step during which the denatured immobilized target proteins are contacted with a digestion solution comprising a protease to form a solution comprising proteolytic peptides. The last step of the method comprises analyzing the solution comprising proteolytic peptides by a mass spectrometry-based technique to detect and/or quantitate the target protein in the biological sample, wherein the analysis utilizes at least one internal standard protein or peptide that is added during one step of the method. Although the methods described below detail the detection and/or quantitation of one target protein, said methods can be readily modified for multiplex detection and/or quantitation of multiple target proteins.

(a) Step A—Target Protein Capture

The first step of the methods disclosed herein comprises capture and enrichment of the target protein from the biological sample. This step comprises adding the biological sample comprising the target protein to an immobilized capture entity, wherein the immobilized capture entity recognizes and binds the target protein, thereby capturing and immobilizing the target protein.

(i) Target Protein

A variety of target proteins can be detected and/or quantitated using the methods disclosed herein. Suitable target proteins include, without limit, antibodies (e.g., polyclonal antibodies, monoclonal antibodies, IgG molecules, IgA molecules, IgD molecules, IgE molecules, IgM molecules, recombinant antibodies, engineered antibodies, chimeric antibodies, and the like), antibody fragments (e.g., heavy chains, light chains, Fab fragments, $F(ab)_2$ fragments, Fc fragments, Fab' fragments, single-chain variable fragments, and fusions of any of the foregoing, e.g., Fc fusion proteins), antibody mimetics, growth factors, interferons, interleukins, other cytokines, protein or peptide hormones, blood clotting factors, anticoagulants, bone morphogenetic proteins, thrombolytics, vaccines, enzymes, engineered protein scaffolds, fusion proteins, therapeutic proteins, diagnostic proteins, fragments of any of the foregoing, or derivatives of any of the foregoing. In specific embodiments, the target protein can be a monoclonal antibody, fragment thereof, or a fusion protein comprising an antibody fragment.

(ii) Biological Sample

The target protein can be detected and/or quantitated in a variety of biological samples. Generally, the biological sample comprises a mixture of the target protein, other proteins, and/or other biological entities (e.g., lipids, nucleic acids, etc.). Non-limiting examples of suitable biological samples include blood, blood serum. blood plasma, amniotic fluid, ascites fluid, biopsy extracts, biopsy fluid, bone extracts, bone marrow aspirations, breast secretions, bronchial secretions, cell culture media, cell extract, cell homogenate, cerebrospinal fluid, cervical secretions, endometrial secretions, feces, gastrointestinal secretions, hemofiltrate, lacrimal fluid, lymph fluid, ovarian cyst secretions, pleural fluid, pre-ejaculatory fluid (Cowper's fluid), prostatic fluid, saliva, semen, seminal fluid, seminal plasma, sputum, sweat, synovial fluid, tissue extracts tissue fluid, tissue homogenate, tears, tumor aspirants, tumor extracts, urine, and vaginal secretions. In specific embodiments, the biological sample can be blood serum or blood plasma.

The biological sample can be used as is, or the biological sample can be purified or semi-purified prior to use in the method. In some embodiments, the biological sample can be used soon after collection. In other embodiments, the biological sample can be stored (e.g., by freezing) prior to use in the method.

In general, the biological sample is in liquid form. In some embodiments, the biological sample can be mixed or diluted with a working solution, wherein the working solution is compatible with protein binding, i.e., binding of target protein to the capture entity. For example, the working solution can be Tris buffered saline, phosphate buffer saline, Tris buffer, phosphate buffer, acetate buffer, or other suitable working solution.

(iii) Immobilized Capture Entity

The immobilized capture entity can be an antibody or fragment thereof, a protein or fragment thereof, a ligand, or an aptamer, wherein the capture entity is capable of binding the target protein. In some embodiments, the capture entity can be an antibody or fragment thereof that recognizes and binds the target protein. For example, the capture entity can be an anti-human IgG antibody that binds human IgGs. In other embodiments, the capture entity can be a protein such as a cytokine, growth factor, hormone, lectin, signaling protein, etc. that binds the target protein. For example, the capture entity can be tumor necrosis factor alpha that binds adalimumab or infliximab. Examples of additional capture entities include, without limit, protein interacting domains such as SH2, SH3, PTB. 14-3-3, FHA, WW, SAM, LIM domains, protein binding domains, peptide ligands, small molecule ligands, carbohydrate ligands, lipid ligands, nucleic acid ligands (i.e., aptamers).

The immobilized capture entity is linked to a solid support by a direct bond, a linker, or an affinity interaction. In general, the direct bond is a covalent bond. Suitable linkers include amino acids, peptides, nucleotides, nucleic acids, organic linker molecules (e.g., maleimide derivatives, N-ethoxybenzylimidazole, biphenyl-3,4',5-tricarboxylic acid, p-aminobenzyloxycarbonyl, and the like), disulfide linkers, and polymer linkers (e.g., PEG). The linker can include one or more spacing groups including, but not limited to alkylene, alkenylene, alkynylene, alkyl, alkenyl, alkynyl, alkoxy, aryl, heteroaryl, aralkyl, aralkenyl, aralkynyl and the like. The affinity interaction can be based on streptavidin-biotin, avidin-biotin, protein A, protein G, protein A/G, protein L, aptarners, ligands, collagen, gelatin, fibronectin, laminin, lectins, or metals.

A variety of solid supports can be used to immobilize the capture entity. Suitable solid supports include plates, well plates, microplates, beads, resins, chips, fibers, and reaction tubes. The solid support can be plastic, polymeric, polymeric comprising embedded magnetic microparticles, membranes (e.g., nitrocellulose), glass, silicon, carbon, gold, stainless steel, or other inert metal.

In specific embodiments, the immobilized capture entity can be a biotinylated antibody attached to a streptavidin-coated solid surface. The streptavidin-coated solid surface can be a well of a multiwell plastic plate.

(iv) Capture Step

The biological sample comprising the target protein is added to the immobilized capture entity and allowed to incubate for a period of time during which the immobilized capture entity captures the target protein from the biological sample to form an immobilized target protein. In general, the incubation period ranges from about 30 minutes to about 18 hours. In some embodiments, the incubation period can range from about 0.5 hour to about 8 hours, from about 1 hour to 4 hours, or from about 1.5 to about 2.5 hours. In other embodiments, the incubation period can range from about 8 hours to about 1 hours. The temperature of the incubation can range from about 4° C. to about 40° C., from about 10° C. to about 35° C., from about 20° C. to about 30° C., or about room temperature (i.e., 22-25° C). In specific embodiments, the incubation can proceed for about 2 hours at room temperature. The immobilized capture entity and the biological sample comprising the target protein can be mixed by shaking, rotating, and/or swirling during the incubation period.

(v) Wash Step

In general, the capture step is followed by one or more wash steps. For this, the biological sample comprising unbound proteins is removed (by decantation or inversion) from the immobilize target protein, and a volume of wash solution is added to the immobilized target protein. The immobilized target protein and wash solution are mixed, and then the wash solution is removed. The wash step can be repeated one or more times. The wash solution can be identical to the working solution mentioned above, which optionally can further comprise a non-ionic surfactant. Non-limiting examples of suitable nonionic surfactants include polysorbate 20 and polyethylene glycol tert-octylphenyl ether.

(b) Step B—Protein Denaturation

The next step of the method comprises adding a denaturation solution comprising an organic solvent to the immobilized target protein to form a denatured immobilized target protein.

A variety of organic solvents can be included in the denaturation solution. Non-limiting examples of suitable organic solvents include methanol, ethanol, isopropanol, trifluoroethanol, acetonitrile, formamide, dimethylformamide, or combinations thereof. In some embodiments, the organic solvent can be methanol. In other embodiments, the organic solvent can be ethanol.

The amount of organic solvent present in the denaturation solution can range from about 30% by volume to about 100% by volume. The balance of the denaturation solution can be water or a buffer solution. In various embodiments, the amount of organic solvent present in the denaturation solution can range from about 30-35% by volume, from about 35-40% by volume, from about 40-45% by volume, from about 45-50% by volume, from about 50-55% by volume, from about 55-60% by volume, from about 60-65% by volume, from about 65-70% by volume, from about 70-75% by volume, from about 75-80% by volume, from about 80-85% by volume, from about 85-90% by volume, from about 90-95% by volume, or from about 95-100% by volume. In specific embodiments, the amount of organic solvent present in the denaturation solution can range from about 40% to about 60% by volume, or from about 45% to about 55% by volume.

The denaturation step is allowed to proceed for a sufficient period of time during which the immobilized target protein is denatured, as well as any protein-based capture entities. During this step, non-covalent interactions are disrupted, thereby unfolding the protein(s) and destroying secondary and tertiary structures. The duration of the denaturation step can range from about 5 minutes to about 60 minutes, from about 6 minutes to about 45 minutes, from about 8 minutes to about 30 minutes, from about 10 minutes to about 20 minutes, from about 12 minutes to about 18 minutes, or from about 14 minutes to about 16 minutes. The temperature of the denaturation step can range from about 4° C. to about 40° C., from about 10° C. to about 35° C., from about 20° C. to about 30 or about room temperature. In specific embodiments, the incubation can proceed for about 15 minutes hours at room temperature. The immobilized target protein and the denaturation solution comprising the organic solvent can be mixed by shaking, rotating, and/or swirling during the incubation period.

The methods disclosed herein are devoid of any washing and/or decanting steps after the denaturation step. Rather, the mixture comprising the denatured immobilized target protein and the denaturation solution comprising the organic solvent is used directly in the digestion step detailed below in section (I)(c).

The methods disclosed herein also are devoid of reducing and/or alkylating steps between the denaturation step and the digestion step. Stated another way, the denatured proteins are not contacted with reducing agents to break disulfide bonds and/or alkylating agents to modify cysteine residues to prevent disulfide bond formation.

(c) Step C—Protein Digestion

The next step of the method comprises adding a digestion solution comprising a protease to the denatured immobilized target protein to form a solution comprising proteolytic peptides.

A variety of proteases can be present in the digestion solution. In general, the proteases that are utilized in the methods disclosed herein are those that cleave proteins into a discrete number of predictable fragments. Such proteases include aminopeptidase M, Arg-C proteinase, Asp-N endopeptidase, carboxypeptidase-A, carboxypeptidase-B, carboxypeptidase-Y, caspases 1-10, chymotrypsin, Clostridiopeptidase B, elastase, enterokinase, Glu-C endoproteinase, factor Xa, glutamyl endopeptidase, granzyme B, Lys-C endopeptidase, papain, pepsin, proline-endopeptidase, pronase, proteinase K, staphylococcal peptidase 1, thermolysin, thrombin, trypsin, and V8-protease. The protease can be a wild-type protein, a recombinant protein, or an engineered recombinant protein. In specific embodiments, the protease can be a trypsin, and in particular, a mammalian trypsin. The trypsin can be treated with N-tosyl-L-phenylalanine chloromethyl ketone (TPCK) to inactivate extraneous chymotryptic activity. In specific embodiments, the trypsin can be from porcine pancreas. In other embodiments, the trypsin can be from bovine pancreas.

The amount of protease in the digestion solution can and will vary, depending upon the identity of the protease. Persons skilled in the art know how to determine the appropriate amount of protease. The digestion solution can comprise a buffer, e.g., Tris, HEPES, phosphate, bicarbonate, or other suitable buffer. In some embodiments, the digestion solution can further comprise a salt (e.g., sodium, potassium and/or calcium salt), a chelator (e.g., EDTA and the like), and/or a nonionic surfactant. The pH of the digestion buffer can range from about 6.5 to about 9.0.

The digestion step is allowed to proceed at a temperature from about 40° C. to about 80° C., from about 50° C. to about 70° C., or from about 55° C. to about 65° C. The duration of the digestion step can range from about 0.5 hour to about 8 hours, from about 1 hour to 4 hours, or from about 1.5 to about 2.5 hours. In specific embodiments, the digestion step is allowed to proceed at about 60° C. for about 2 hours. During the incubation period, the protease digests the immobilized target protein and releases proteolytic peptides in the surrounding digestion solution.

In some embodiments, the denaturation step and the digestion step can be combined by simultaneously adding the denaturation solution comprising the organic solvent and the digestion solution comprising the protease to the immobilized target protein after the capture step. Alternatively, a combined denaturation and digestion solution can be prepared by mixing the appropriate amounts of the organic solvent and the protease to a digestion solution, and the combined solution can be added to the immobilized target protein after the capture step. The immobilized target protein and combined denaturation/digestion solution(s) are incubated under digestion conditions as detailed above.

After the digestion step, the solution comprising the proteolytic peptides is used directly for a mass spectrometry-based analytical technique. The solution comprising the proteolytic peptides is not subjected to a clean-up process such as solid phase extraction.

(d) Internal Standards

The methods disclosed herein are quantitative because at least one internal standard is added during one step of the process. As used herein, an internal standard is a stable isotope-labeled protein or peptide comprising at least one peptide sequence that is unique to the target protein. Such unique sequences are termed "surrogate" or "reporter" peptides, and are used for quantitation and monitoring during the mass spectrometry-based analysis.

In some embodiments, the internal standard is a stable isotope-labeled full length version of the target protein, wherein said internal standard protein is added during step (a) of the method. Adding internal standard proteins during the capture step normalizes all processing variation throughout the method. In other embodiments, the internal standard is a stable isotope-labeled protein comprising universal peptide sequences present in the target protein. Such internal standards are call "universal" internal standards, and are added during step (a) of the method. Internal standards added during the capture step are also captured by the immobilized capture entity.

In still other embodiments, the internal standard is a stable isotope-labeled and cleavable version of a surrogate peptide. A cleavable version of the surrogate peptide comprises extra amino acids of the sequence of the surrogate concatenated at each end, such that cleavage by the protease produces a stable isotope-labeled version of the surrogate peptide. Cleavable versions of the surrogate peptide are also called "winged" peptide internal standards, and are added prior to digestion with the protease of step (c).

In additional embodiments, the internal standard is a stable isotope-labeled version of a surrogate peptide. Stable isotope-labeled versions of the surrogate peptide are prior to or after the protease digestion of step (c).

(e) Step D—Mass Spetrometric Analysis

The last step of the method comprises analyzing the proteolytic peptides by a mass spectrometry-based technique to detect and/or quantitate the target protein in the biological sample. Such an analysis depends upon identification of one or more appropriate surrogate peptides for quantitation and monitoring. Surrogate peptides are unique to the target protein and respond well in mass spectrometry (e.g., good ionization, etc.). Quantitation is performed by measuring the one or more surrogate peptides relative to the one or more stable isotope-labeled internal standards added during the method using conventional stable isotope dilution methods.

Suitable mass spectrometry-based techniques include liquid chromatography-tandem mass spectrometry (LC-MS/MS), liquid chromatography tandem mass spectrometry (LC-MS/MS) with multiple reaction monitoring (MRM), liquid chromatography-tandem mass spectrometry (LC-MS/MS) with selective reaction monitoring (SRM), two-dimensional-liquid chromatography-tandem mass spectrometry (2D-LC-MS/MS), liquid chromatography-mass spectrometry (LC-MS), or capillary zone electrophoresis-electrospray ionization-tandem mass spectrometry (CZE-ESI-MS/MS). In specific embodiments, the analytical method is liquid chromatography-tandem mass spectrometry (LC-MS/MS) with multiple reaction monitoring (MRM). The chromatography conditions and mass spectrometry settings can and will vary depending upon the peptides being analyzed.

The proteolytic peptides are analyzed by directly introducing the solution comprising the proteolytic peptides into the analytical system. For example, an aliquot of the solution comprising the proteolytic peptides can be injected into a liquid chromatography-mass spectrometry system. Appropriate calibration and quality control standards are also included in the analysis.

The methods disclosed herein have a lower limit of quantitation (LLOQ) that is less than about 100 ng/mL of target protein in the biological sample. In some embodiments, the LLCM can be less than about 30 ng/mL, less than about 10 ng/mL, less than about 3 ng/mL, less than about 1 ng/mL, less than about 0.3 ng/mL, less than about 0.1 ng/mL, less than about 0.03 ng/mL, or less than about 0.01 ng/mL of target protein in the biological sample.

In some embodiments, the measured peptides can be compared to peptide masses, product ion spectra, or sequence query from in silica digestion of protein databases using suitable protein search engines to identify proteins in the biological sample.

(II) Kits

Another aspect of the present disclosure provides kits for detecting and/or quantitating target proteins in biological samples. In general, the kits can comprise a denaturation solution or components to prepare a denaturation solution as described above in section (I)(b), and a digestion solution or components to prepare a digestion solution as described above in section (I)(c). The kits can further comprise a capture entity directed to the target protein of interest (as described above in section (I)(a)(iii)). The capture entity can be linked to a solid support and provided as such in the kit. Alternatively, the capture entity can be provided in a free form along with means for linking the capture entity to a solid support. For example, the capture entity can be biotinylated antibody, which can be provided along with a streptavidin-coated solid support (e.g., a 96 well plate) or streptavidin for coating a solid support. The kits also can contain at least one stable-isotope labeled internal standard protein, as described above in section (I)(d). In additional embodiments, the kits can further comprise working solutions and wash solutions for use during the target protein capture step of the method (see sections (I)(a)(ii) and (I)(a)(v), respectively).

The kits provided herein generally include instructions for capturing and detecting/quantitating the protein of interest. Instructions included in the kits may be affixed to packaging material or may be included as a package insert. While the instructions are typically written or printed materials, they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" can include the address of an interest site that provides the instructions.

(III) Applications

The methods and kits provide herein have a variety of uses applications. Non-limiting examples of suitable applications include preclinical verification of biomarkers, biotherapeutic assays, clinical assays, diagnostic assays, therapeutic monitoring assays, pharmacokinetic studies, non-clinical studies, and so forth. The methods can be for diagnostic, therapeutic, clinical, industrial, and/or research applications.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

The term "about," particularly in reference to a given quantity, is meant to encompass deviations of plus or minus five percent.

The term "capture entity" refers to an entity capable of binding to and capturing the target protein.

The terms "protein" and "polypeptide" refer to chains of amino acids linked by peptide bonds, regardless of post-translational modification (e.g., phosphorylation, glycosylation, acetylation, and the like).

As various changes could be made in the above-described cells and methods without departing from the scope of the invention, it is intended that all matter contained in the above description and in the examples given below, shall be interpreted as illustrative and not in a limiting sense.

EXAMPLES

The following examples illustrate certain aspects of the invention.

Example 1: Optimization of Proteolytic Digestion

To evaluate the efficiency of several different digestion protocols, first, immunoaffinity enrichment of 100 μL of 0.64 μg/mL of unlabeled Adulimumab antibody in monkey serum was performed. Then, the antibody was digested using three different digestion protocols.

1—Rapid high temperature digestion without denaturation protocol. To well 1 was added 190 μL of 50 mM ammonium bicarbonate digestion buffer and 10 μg of trypsin. The sample was incubated for 2 hr at 70° C. (no denaturation was performed).

2—Conventional reduction, alkylation, and digestion protocol. To well 2 was added 100 μL of 10 mm Tris(2-carboxyethyl)phosphine hydrochloride and incubated for 30 min at 37° C. After reduction, the sample was alkylated by adding 20 μL of 100 mM IAA and incubating for 30 min at RT. Then, 70 μL of 50 mM ammonium bicarbonate digestion buffer and 10 μg of trypsin were added and incubated for 16 hr at 37° C.

3—Rapid high temperature digestion with denaturation protocol (i.e., optimized protocol). To well 3 was added 50 μL of 50% MeOH and incubated for 15 min, Then 136 μL of 50 mM ammonium bicarbonate digestion buffer, 4 μL of 1M $CaCl_2$ and 10 μg of trypsin were added and incubated for 1 hr at 60° C.

The total amount of 25 ng of predigested SIL-Adulimumab internal standard was added to each well after the trypsin digestion. All samples were prepared in duplicate, and analyzed via LC-MS/MS. As shown in FIG. 1, denaturation of antibody (protocol #3) significantly improves the signal intensity and enables more rapid and simplified sample preparation compared to conventional protocols.

Figure 2A:
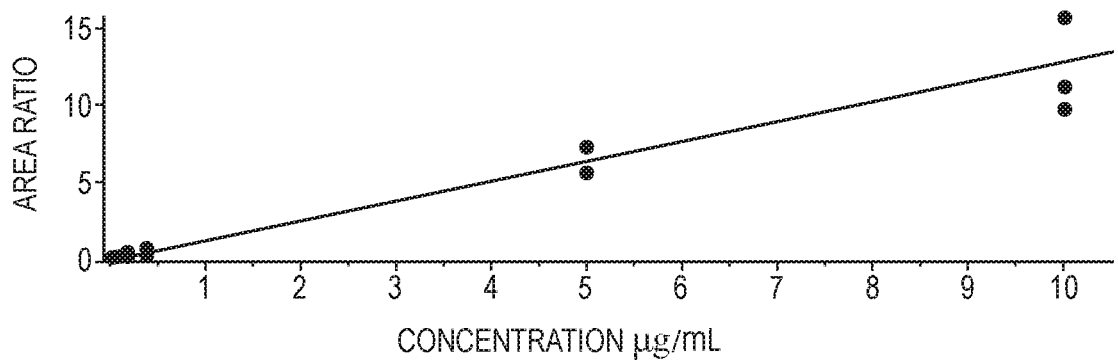
FIG. 2A presents a calibration curve of digested standards prepared using conventional protocol without reduction and alkylation steps using 100 μL of monkey serum.
Figure 2B:
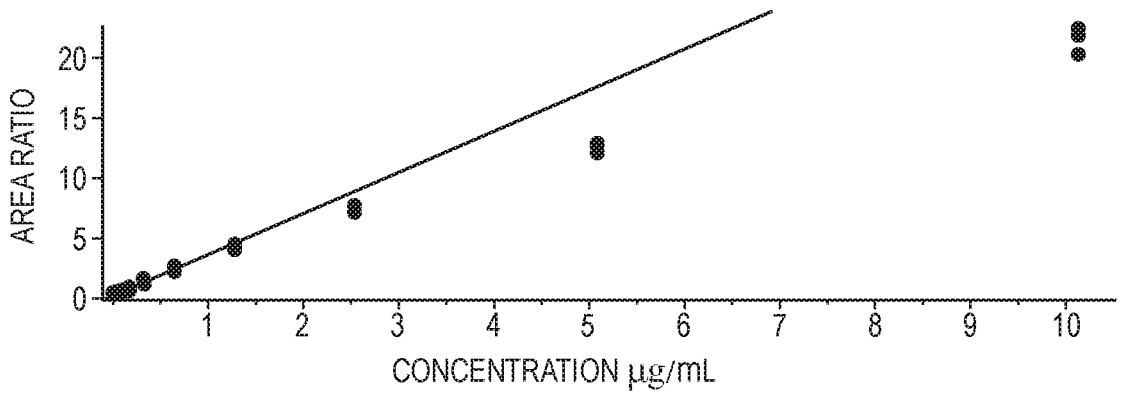
FIG. 2B shows a calibration curve of digested standards prepared using the process disclosed herein and 100 μL of monkey serum.
Figure 2C:
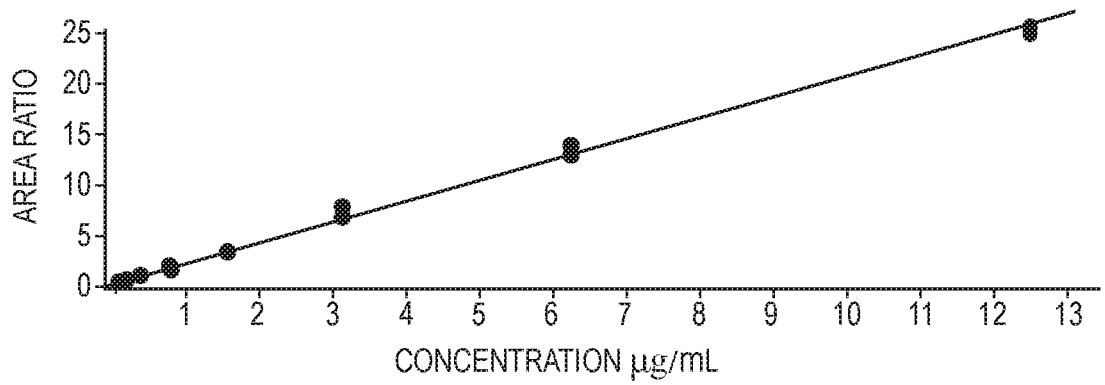
FIG. 2C presents a calibration curve of digested standards prepared using the process disclosed herein and 5 μL. of monkey serum.

Calibration curves of digested standards were prepared using the conventional protocol without reduction and alkylation steps or the optimized protocol. FIG. 2A presents the calibration curve of digested standard (VVSVLTVLHQDWLNGK: SEQ ID NO:1) prepared using conventional protocol without reduction and alkylation steps using 100 μL of monkey serum. All % CV's were unsuitable. FIG. 2B shows (the calibration curve of digested standard (TTPPVLDSDGSFFLYDK: SEQ ID NO:2) using optimized protocol and 100 μL of monkey serum. Assay range is 0.005-1.28 μg/mL with % CV<20 and accuracy of ±20. Nonlinear in higher concentration of 1.28-12.5 μg/mL (accuracy>±20). FIG. 2C presents the calibration curve of digested standard (TIPPVLDSDGSFFLYDK; SEQ ID NO:2) using optimized digestion protocol and 5 μl of monkey serum. Assay range is 0.1-12.5 μg/mL with % CV<20 and accuracy of ±20. Thus, using the optimized digestion protocol, a linear quantification range of 0.1 to 12.5 μg/mL with % CV<20 for triplicated samples and accuracy of ±20% is demonstrated with just 5 μL of serum.

Example 2. Denaturation Using Various Organic Solvents

Figure 3:
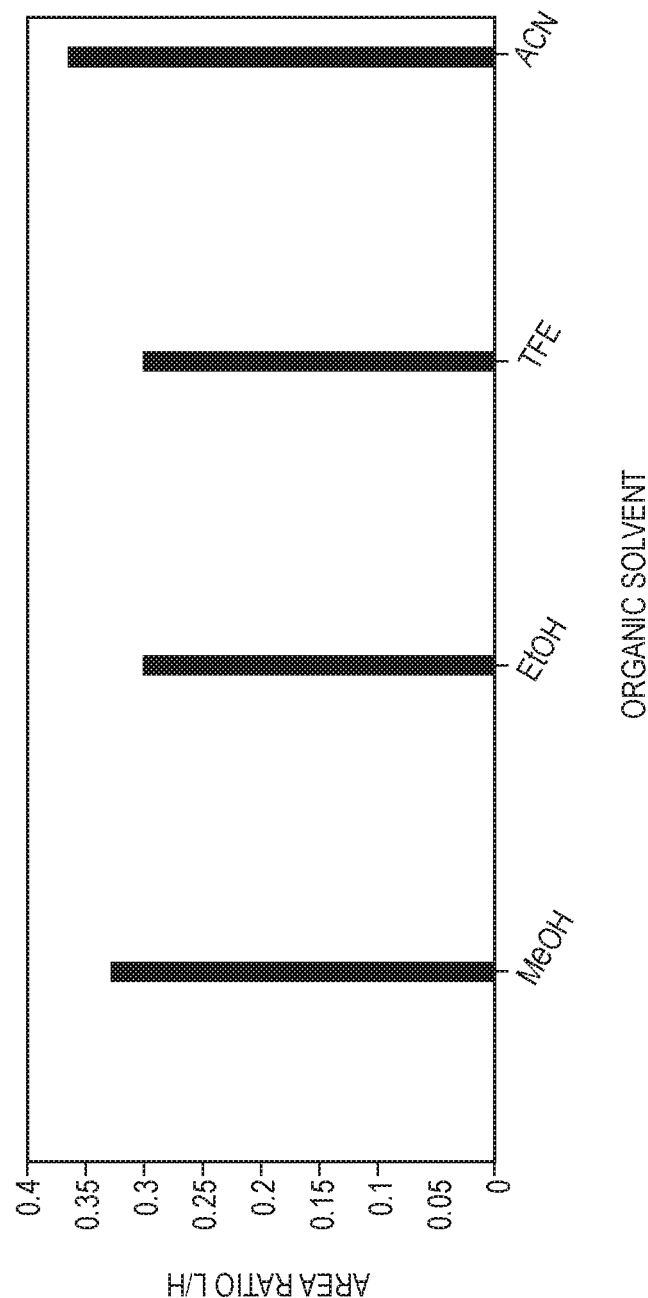
FIG. 3 shows the efficiency of digestion using different denaturation organic solvents in conjunction with rapid high temperature digestion.

The optimized digestion protocol was performed in the presence of various organic solvents after immunoaffinity enrichment of 5 μL of 1.25 μg/mL of unlabeled Adulimumab antibody in monkey serum. A volume of 50 μL of 50% of organic solvent (i.e., methanol, ethanol, trifluoroethanol (TFE), or acetonitrile (ACN)), 150 μL of ammonium bicarbonate digestion buffer. 5 μg of trypsin were added. The digestion was performed for 2 hr at 60° C. The predigested SIL-Adulimumab internal standard (25 ng) was added to each well after the trypsin digestion. The samples were prepared in duplicate. The % CV of duplicate samples was <5%. As shown in FIG. 3, the results demonstrate that the tested organic solvents behave the same as denaturation solution (50% MeOH) in the optimized digestion protocol. The experiment was performed in both 50 mM Tris and 50 mM ammonium bicarbonate, and the results were similar.

What is claimed is:

1. A method for detecting and/or quantitating a target protein in a biological sample, the method comprising:
    a) adding the biological sample comprising the target protein to an immobilized capture entity to capture the target protein, thereby forming an immobilized target protein;
    b) adding a denaturation solution comprising an organic solvent to the immobilized target protein to form a denatured immobilized target protein;
    c) digesting the denatured immobilized target protein at a temperature from 40° C. to 80° C. with a digestion solution comprising a protease to form a solution comprising proteolytic peptides, wherein said method is devoid of a reducing step and an alkylating step prior to step (c); and
    d) analyzing the solution comprising proteolytic peptides by a mass spectrometry-based technique to detect and/or quantitate the target protein in the biological sample, wherein the analyzing utilizes at least one internal standard protein or peptide that is added during one step of the method, and wherein said solution comprising proteolytic peptides is not subject to a clean-up process prior to analyzing the solution by the mass spectrometry-based technique.

2. The method of claim 1, wherein the immobilized capture entity is an antibody, an antibody fragment, a protein, a protein fragment, a ligand, or an aptamer.

3. The method of claim 1, wherein the immobilized capture entity is linked to a solid support by a direct bond, a linker, or an affinity interaction.

4. The method of claim 3, wherein the affinity interaction comprises streptavidin-biotin, protein A, protein G, protein AIG, protein L, an aptamer, or a ligand.

5. The method of claim 3, wherein the solid support is a well plate, a microplate, a bead, a resin, a chip, a fiber, or a reaction tube.

6. The method of claim 1, wherein the immobilized capture entity is a biotinylated antibody attached to a streptavidin-coated solid support.

7. The method of claim 1, wherein the target protein is an antibody, an antibody fragment, or a fusion protein comprising an antibody fragment.

8. The method of claim 1, wherein the biological sample is blood serum or blood plasma.

9. The method of claim 1, wherein step (a) is allowed to proceed for about 1 hour to about 4 hours at room temperature.

10. The method of claim 1, wherein step (a) is followed by at least one washing step.

11. The method of claim 1, wherein the organic solvent in the denaturation solution at step (b) is methanol, ethanol, isopropanol, trifluoroethanol, acetonitrile, formamide, dimethylformamide, or a combination thereof, and is present at about 30% to about 100% by volume.

12. The method of claim 11, wherein the organic solvent is methanol or ethanol and is present at about 40% to about 60% by volume.

13. The method of claim 1, wherein step (b) is allowed to proceed for about 5 minutes to about 60 minutes at room temperature.

14. The method of claim 1, wherein the protease in the digestion solution at step (c) is a trypsin.

15. The method of claim 14, wherein the trypsin is a mammalian trypsin.

16. The method of claim 1, wherein step (d) is allowed to proceed for about 1 hour to about 4 hours at about 50° C. to about 70° C.

17. The method of claim 1, which is devoid of a washing step and/or a decanting step between steps (b) and (c).

18. The method of claim 1, wherein steps (b) and (c) are combined by simultaneously adding the denaturation solution comprising the organic solvent and the digestion solution comprising the protease to the immobilized target protein.

19. The method of claim 18, further comprising incubating for about 1 hour to about 4 hours at about 50° C. to about 70° C.

20. The method of claim 1, wherein the at least one internal standard protein or peptide is added during step (a) and is a stable isotope labeled version of the target protein or a stable isotope-labeled protein comprising universal peptide sequences present in the target protein.

21. The method of claim 1, wherein the at least one internal standard protein or peptide is added prior to step (c) and is a stable isotope labeled and cleavable version of a surrogate peptide.

22. The method of claim 1, wherein the at least one internal standard protein or peptide is added prior to or after step (c) and is a stable isotope-labeled version of a surrogate peptide.

23. The method of claim 1, wherein the mass spectrometry-based technique at step (d) is liquid chromatography tandem mass spectrometry (LC-MS/MS).

24. The method of claim 1, which has a lower limit of quantitation that is less than about 50 ng/mL.

25. The method of claim 24, wherein the lower limit of quantitation is less than about 10 ng/ml.

* * * * *